United States Patent
Tkabladze et al.

(10) Patent No.: US 10,062,467 B2
(45) Date of Patent: Aug. 28, 2018

(54) X-RAY GENERATOR OUTPUT REGULATION

(71) Applicant: Schlumberger Technology Corporation, Sugar Land, TX (US)

(72) Inventors: Avtandil Tkabladze, Sugar Land, TX (US); Justin Dale Mlcak, Richmond, TX (US); Sicco Beekman, Houston, TX (US); Matthieu Simon, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/373,630

(22) Filed: Dec. 9, 2016

(65) Prior Publication Data

US 2017/0169909 A1   Jun. 15, 2017

(51) Int. Cl.

| G01V 5/12 | (2006.01) |
|---|---|
| G21K 1/10 | (2006.01) |
| G01N 23/223 | (2006.01) |
| G01V 5/08 | (2006.01) |
| H01J 35/00 | (2006.01) |

(52) U.S. Cl.
CPC ............. *G21K 1/10* (2013.01); *G01N 23/223* (2013.01); *G01V 5/08* (2013.01); *G01V 5/12* (2013.01); *H01J 35/00* (2013.01); *G01N 2223/20* (2013.01); *G01N 2223/616* (2013.01)

(58) Field of Classification Search
CPC ........... G01N 21/6486; G01N 21/8507; G01N 23/223
See application file for complete search history.

(56) References Cited

U.S. PATENT DOCUMENTS

| 4,524,273 | A | 6/1985 | Hubner |
|---|---|---|---|
| 6,649,914 | B1 | 11/2003 | Moorman et al. |
| 7,564,948 | B2 | 7/2009 | Wraight et al. |
| 7,668,293 | B2 | 2/2010 | Wraight et al. |
| 7,960,687 | B1 | 6/2011 | Simon et al. |
| 7,991,111 | B2 | 8/2011 | Wraight et al. |
| 2007/0274443 | A1 | 11/2007 | Groves et al. |
| 2009/0161823 | A1 | 6/2009 | Groves et al. |
| 2011/0002443 | A1 | 1/2011 | Wraight et al. |

(Continued)

FOREIGN PATENT DOCUMENTS

WO   2012050725 A2   4/2012

OTHER PUBLICATIONS

International Search Report and Written Opinion issued in International Patent Application No. PCT/US2015/065001 dated Sep. 7, 2016; 10 pages.

(Continued)

*Primary Examiner* — Don Wang
(74) *Attorney, Agent, or Firm* — Michael Dae

(57) ABSTRACT

The techniques and device provided herein relate to regulating a source generator in an X-ray based equipment. In particular, an X-ray system is provided that comprises an X-ray generator and a reference detector system that regulates the output of the X-ray generator. The reference detector system comprises a direct channel that allows at least a portion of the photons to directly reach the detector crystal and a plurality of fluorescent channels, such that photon flux entering the reference detector from the fluorescent channels is negligibly impacted by variations of beam spots, shapes and/or positions.

15 Claims, 8 Drawing Sheets

(56) References Cited

U.S. PATENT DOCUMENTS

2011/0112810 A1   5/2011   Scoullar et al.
2011/0191027 A1   8/2011   Pfutzner et al.
2014/0355737 A1   12/2014  Korkin et al.

OTHER PUBLICATIONS

International Search Report and written opinion issued in the related PCT application PCT/US2016/064494, dated Feb. 6, 2017 (8 pages).

X-RAY GENERATOR OUTPUT REGULATION

This application claims priority to International Patent Application No. PCT/US2015/065001 filed Dec. 10, 2015, the entirety of which is incorporated herein by reference.

BACKGROUND

This application claims priority to International Patent Application No. PCT/US2015/065001 filed Dec. 10, 2015, the entirety of which is incorporated herein by reference.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Numerous well logging tools are used to identify characteristics of geological formations where wells are drilled. For example, properties such as a density and/or photoelectric factors of the formation may be measured by downhole well-logging tools.

Traditionally, radioisotopic sources, such as radiocaesium (also referred to as Caesium-137 (Cs-137) have been used for density measurement in well-logging tools. Indeed, radioisotopic sources may provide a stable flux output and relatively high energy of source photons that are suitable for consistent density measurement. Unfortunately, however, the use of chemical sources in a well-logging application may be undesirable, as strict operational standards and procedures may regulate such practices. These regulations may add operational burdens to downhole development. Accordingly, new non-chemical methods that provide reliable density measurements may be desirable.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the disclosure relate to using X-ray measurements to determine density and/or photoelectric factors of a well formation, by downhole well-logging tools. More particularly, the current embodiments relate to stabilization of an electronic photon generator used in X-ray measurements by regulating the source strength based upon signals detected by a reference detector of the X-ray measurement system.

Some embodiments relate to a downhole tool comprising an X-ray system and a reference detector system. The X-ray system comprises a generator that produces a source stream of electrons and accelerates them to a beam spot on a target to generate photons. The reference detector system comprises a photomultiplier tube (PMT) configured to detect and provide an amount and energy of the source stream of photons that reach it, a detector crystal configured to interact with photons and produce scintillation light before they reach the PMT, a direct channel configured to allow at least a portion of the stream of photons to directly reach the detector crystal, a filter configured to reduce a low energy part of a resultant spectrum of the PMT, and a plurality of fluorescent channels positioned substantially symmetrically, such that photon flux entering the reference detector from the fluorescent channels is negligibly impacted by variations of the beam spot.

Some embodiments relate to a downhole tool comprising an X-ray system and a reference detector system. The X-ray system comprises a generator that produces a source stream of electrons and accelerates the electrons to a beam spot on a target, where they generate photons. The reference detector system comprises a photomultiplier tube (PMT) configured to detect and provide an amount and energy of the source stream of photons that reach it, a detector crystal configured to interact with photons and produce scintillation light before they reach the PMT, a direct channel configured to allow at least a portion of the stream of photons to directly reach the detector crystal, a filter configured to reduce a low energy part of a resultant spectrum of the PMT, and a fluorescence material structure positioned and angled to generate fluorescence that reaches the detector crystal via at least one fluorescent channel or aperture, such that a photon flux entering the reference detector via the fluorescent channel or aperture is negligibly impacted by variations in the position or shape of the beam spot.

Some embodiments relate to a method of constructing a downhole tool with X-ray output regulation. The method comprises constructing two or more pieces of an internal shield of the downhole tool, creating a fluorescence channel in at least one of the pieces via a milling operation, and after creating the fluorescence channels, assembling the two or more pieces to form a complete internal shield.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Many downhole tools used for logging wells drilled for hydrocarbon production, $CO_2$ sequestration or other purposes obtain measurements of the formation surrounding the wells. As mentioned above, traditional density measurement systems for downhole tools may use highly-regulated radioisotopes for obtaining formation density measurements that may provide increased operational burdens. Accordingly, this disclosure describes systems and methods that may stabilize source X-ray source energies and output flux, such that X-ray technology may facilitate downhole density and/or photoelectric factor measurements.

Figure 1:
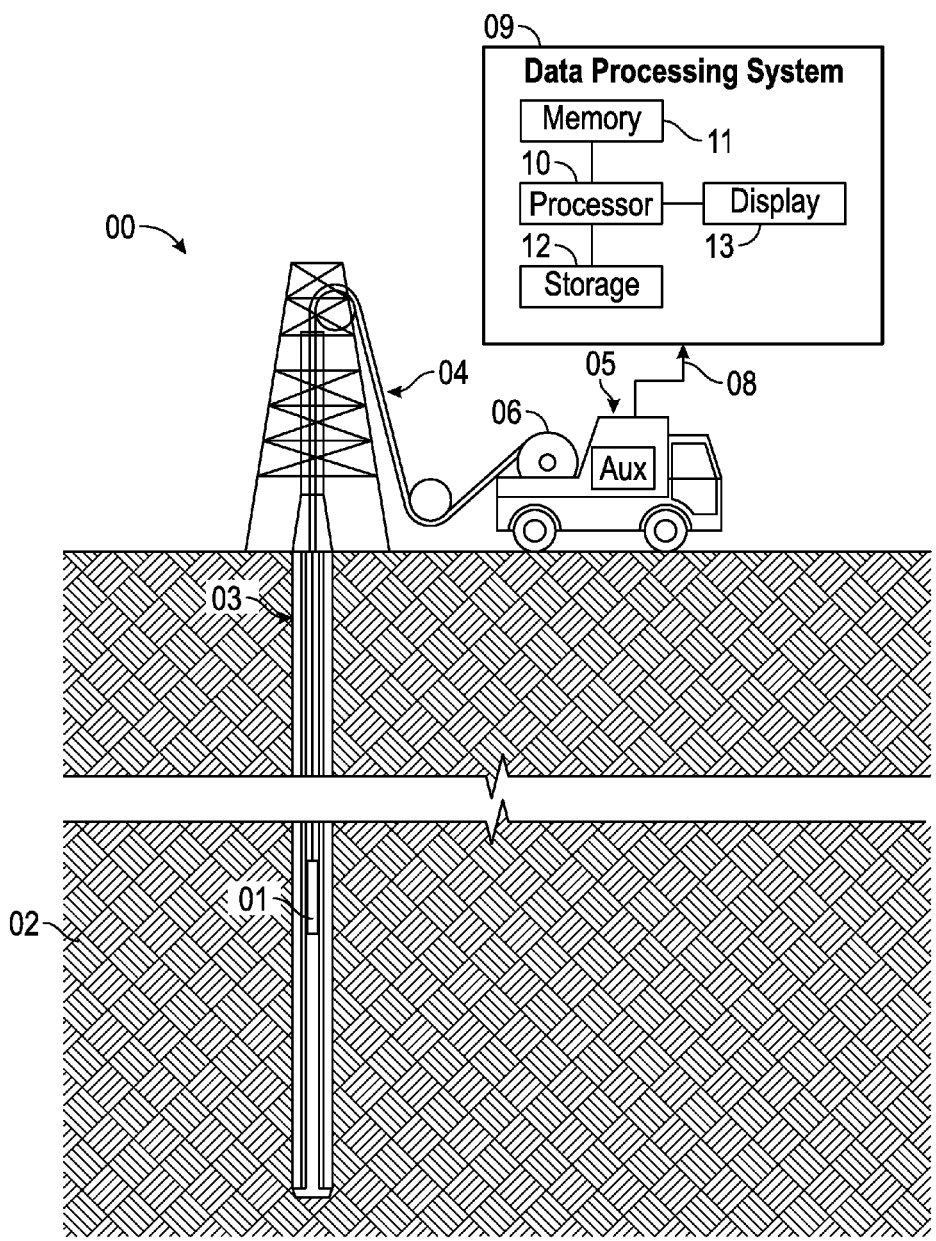
FIG. 1 is a schematic diagram of a well-logging system that uses a source-regulated X-ray equipped well-logging tool, in accordance with an embodiment.

With this in mind, FIG. 1 is a schematic diagram illustrating a well-logging system 00 that may obtain logging measurements, using an X-ray system 14 of FIG. 2, where the X-ray system 14 is regulated based upon filtered spectrum data, as described in more detail below. The well-logging system 00 may be conveyed through a geological formation 02 via a wellbore 03. The downhole tool 01 is conveyed on a cable 04 via a logging winch system 05. Although the logging winch system 05 is schematically shown in FIG. 1 as a mobile logging winch system carried by a truck, the logging winch system 05 may be substantially fixed (e.g., a long-term installation that is substantially permanent or modular). Any suitable cable 04 for well logging may be used. The cable 04 may be spooled and unspooled on a drum 06 and an auxiliary power source 07 may provide energy to the logging winch system 05 and/or the downhole tool 01.

Although the downhole tool 01 is described as a wireline downhole tool, it should be appreciated that any suitable conveyance may be used. For example, the downhole tool 01 may instead be conveyed as a logging-while-drilling (LWD) tool as part of a bottom hole assembly (BHA) of a drill string, conveyed on a slickline or via coiled tubing, and so forth. For the purposes of this disclosure, the downhole tool 01 may be any suitable measurement tool that obtains multidimensional measurements through depths of the wellbore 03.

Many types of downhole tools may obtain measurements in the wellbore 03. For each depth of the wellbore 03 that is measured, the downhole tool 01 may generate density and/or photoelectric factor measurements.

The downhole tool 01 may provide such measurements 08 to a data processing system 09 via any suitable telemetry (e.g., via electrical signals pulsed through the geological formation 02 or via mud pulse telemetry). The data processing system 09 may process the measurements 08 to identify patterns in the measurements 08. The patterns in the multi-dimensional measurements 08 may indicate certain properties of the wellbore 03 (e.g., porosity, permeability, relative proportions of water and hydrocarbons, and so forth) that would be otherwise indiscernible by a human operator.

To this end, the data processing system 09 thus may be any electronic data processing system that can be used to carry out the systems and methods of this disclosure. For example, the data processing system 09 may include a processor 10, which may execute instructions stored in memory 11 and/or storage 12. As such, the memory 11 and/or the storage 12 of the data processing system 09 may be any suitable article of manufacture that can store the instructions. The memory 11 and/or the storage 12 may be ROM memory, random-access memory (RAM), flash memory, an optical storage medium, or a hard disk drive, to name a few examples. A display 13, which may be any suitable electronic display, may provide a visualization, a well log, or other indication of properties of the wellbore 03 based on the multidimensional measurements 08.

Figure 2:
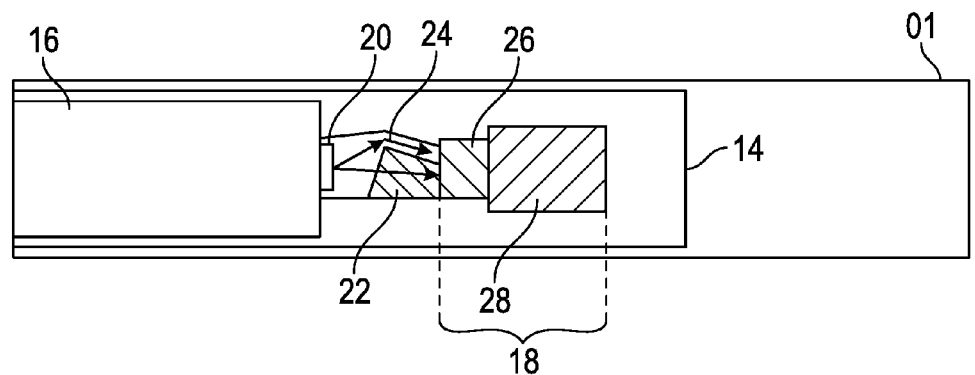
FIG. 2 is a schematic diagram of a well-logging tool that may obtain logging measurements using an X-ray system that is regulated based upon filtered spectrum data, in accordance with an embodiment.

Turning now to a detailed discussion of the well-logging tool 01, FIG. 2 is a schematic diagram of a well-logging tool 01 that may obtain logging measurements. As mentioned above, measurement systems not using chemical (or radio-isotopic) sources of radiation may provide certain benefits in downhole operations. Accordingly, the current well-logging tool 01 is equipped with an X-ray system 14 that operates a generator 16 (e.g., an X-ray generator) at high voltage (e.g., more than 250 keV). To avoid instability or drift of the generator in the X-ray system 14, the X-ray system is regulated based upon filtered spectrum data, in accordance with an embodiment.

As mentioned above, the X-ray generator can be used in downhole applications to obtain measurements for the formation 02, including, but not limited to, density and photoelectric factors. To measure downhole density and/or photoelectric factors, the downhole well-logging tool 01 uses the source 16 to provide x-rays and a measurement detector to detect x-rays. Emitted photons from the generator 16 undergo interaction with formation 02 elements, causing the photons to scatter or be absorbed by the formation 02. Some of the scattered photons return back to the detector (or multiple detectors) (not shown) mounted in the logging tool 01. The density and photoelectric factors are derived from the photon counts and energies that are observed at the detectors.

The principle of an electronic X-ray generator is based on the so-called bremsstrahlung effect. The high energy electrons traveling in the electromagnetic field emit photons when they strike a target 20. The emitted photon spectrum is rather broad, and the energy is less than the incident electron energy. The target 20 thickness is large enough to stop the majority of electrons in the incident electron beam.

Unfortunately, unlike radioisotopic sources, the output of generator source 16 may not be stable. Fluctuation of high voltage and electron beam current can change the energy spectra of emitted photons. In other words, both the energy and the intensity of source 16 photons can vary. If the source strength is not regulated, additional uncertainty is introduced in the count rates of measured photons, as the number and energy of source photons may vary over time. Indeed, the amount of photons reaching the detectors after passage through the formation 02 depends on the energy of photons emitted by source 16 into the formation as well as the flux intensity. Accordingly, as may be appreciated, the accuracy of the formation 02 density measurement can suffer significantly as the energy and intensity of the photon source varies. Therefore, the accuracy of the density measurements may be vastly improved by regulating the output of the source 16. The required accuracy of the regulation depends on the specification of the measurement.

One mechanism for regulating the X-ray generator (e.g., source 16) high voltage and beam current may utilize a portion of the photons that travel through the logging tool 01. This portion of photons may be detected by a dedicated reference detector 18. If the reference detector 18 and the path of source photons from the radiation target 20 to this detector 18 are properly shielded, the spectrum of detected photons is independent from environmental variables and can be used for generator source 16 regulation.

As illustrated in FIG. 2, the generator source 16, generator target 20, and reference detector 18 are contained inside the logging tool 01. The reference detector 18 is shielded, such that the scattered photons produced from the borehole or formation 02 cannot reach it. In the current embodiment, a special filter 22 is positioned between the target 20 and the reference detector 18. In some embodiments, the filter 22 may be manufactured from a high density and high Z (e.g., high atomic number) material, like tungsten, lead, or any heavy material. The high density and high z material may act to attenuate photons effectively, resulting in only part of the source radiation reaching the reference detector 18. For example, the filter 22 may attenuate the low energy part of the source photon spectrum and passes only the high energy tail to the detector 18 (e.g., through a direct channel 23).

In addition, in the current embodiment, the logging tool 01 includes an indirect path (e.g., channel 24) from the target 20 to a detector crystal 26 of the reference detector 18. The source photons hitting the wall of the channel 24 create a fluorescent emission. The fluorescent peak has relatively low energy. The detector crystal 26 may reduce sensitivity to background radiation, while allowing a photomultiplier tube (PMT) 28 to detect and provide an amount of photons that reach it.

Figure 3:
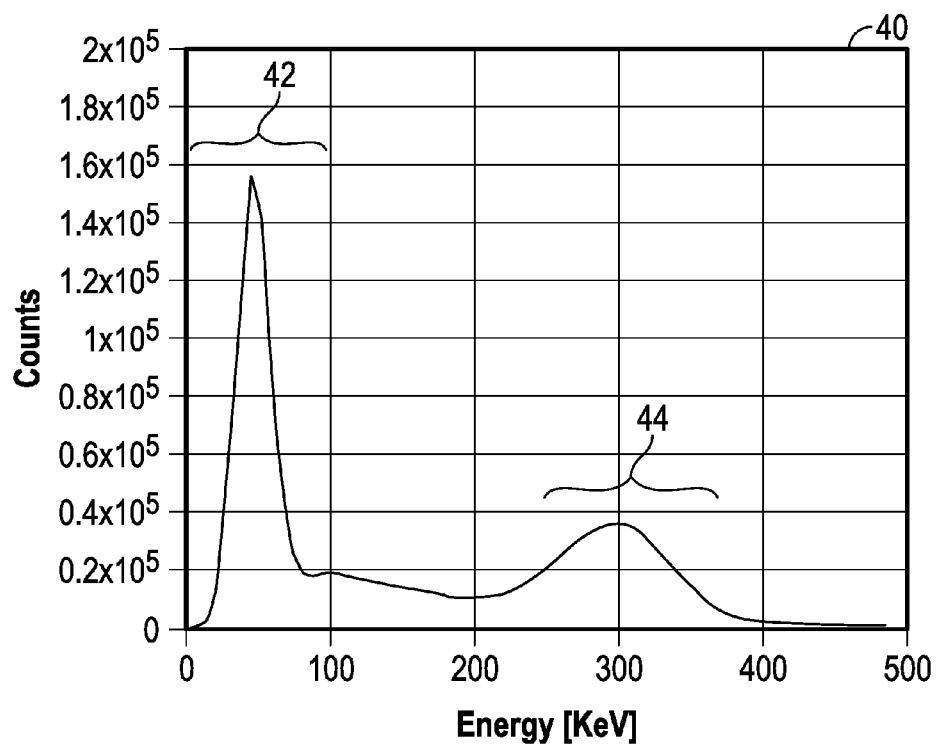
FIG. 3 is a chart illustrating an example of spectrum data obtained via the well-logging tool of FIG. 1, in accordance with an embodiment.

For example, FIG. 3 is a chart illustrating an example of spectrum data 40 obtained via the PMT 28 of the well-logging tool 01 of FIG. 1, in accordance with an embodiment. As illustrated, the final spectrum of detected photons looks like a two peak distribution. The low energy peak 42 is created by the fluorescent photons produced via the channel 24 of FIG. 1. The high energy peak 44 is created by the high energy tail of the initial spectra with the low energy part removed by the filter 22. In some embodiments, the counts provided by the spectrum data may be summed in two bins to provide two numbers $W_{LE}$ and $W_{HE}$, which correspond to the integration of respectively the low and high energy parts of the spectrum.

Figure 4:
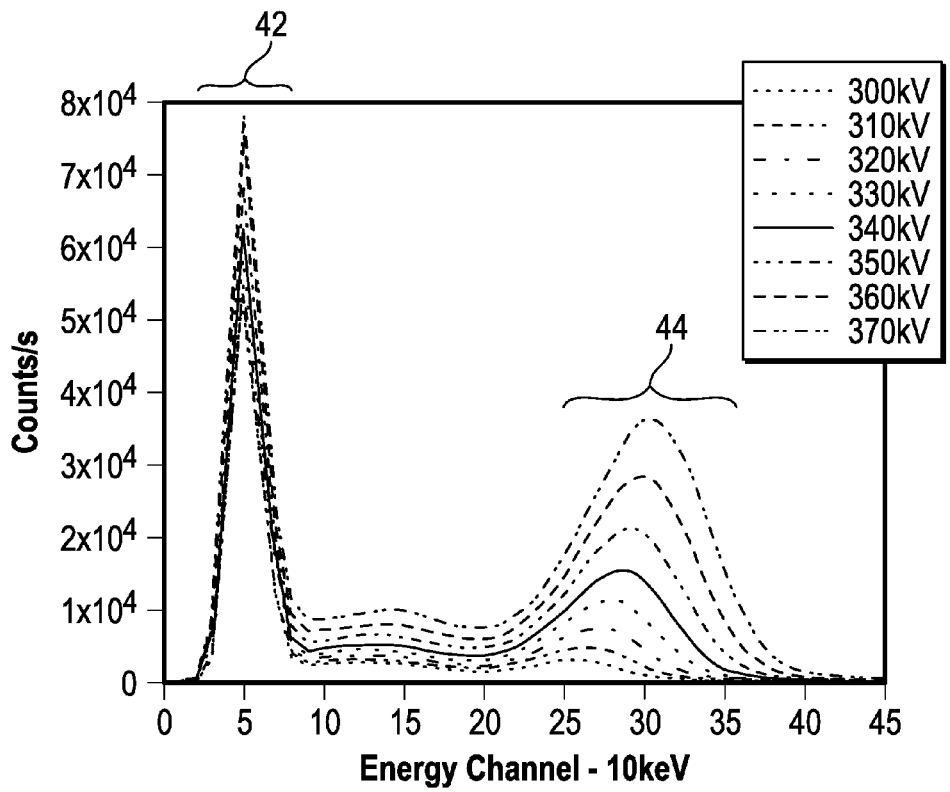
FIG. 4 is a chart illustrating an example of multiple sets of spectrum data for different accelerator voltages, in accordance with an embodiment.

The total counts of the reference detector 18 are proportional to the electron beam current if the high voltage of the generator source 16 is fixed. Accordingly, the ratio of the count rates in the low energy and high energy windows ($W_{LE}/W_{HE}$) is sensitive to the voltage of the generator source 16 of FIG. 2. Thus, fixing the counts of the low energy and high energy windows of the reference detector 18 may act to stabilize the electron beam current and end-point energy of the generator source 16. For example, in FIG. 4, the high energy components ($W_{HE}$) 44 of the spectrum are very sensitive to the high voltage. The low energy components ($W_{LE}$) 42 are proportional to the beam current, but also depend to some extent on the high voltage. In FIG. 4, $W_{LE}$ and $W_{HE}$ would be the total count rate between 0 and 120 keV and 200 and 400 keV, respectively.

This scheme works well when the electron beam spot on the target 20 (i.e. the photon emission point) does not move. Unfortunately, beam spot movement may occur during operation of the downhole tool 01 and/or as a consequence of tool-to-tool variation. When the beam spot moves, the effective geometry of the shielding setup changes, which may distort the reference detector spectra. For example, the apparent high voltage and beam current derived from the reference detector 18 window counts may be different from the nominal values of high voltage and current used to stabilize the generator output.

The systems and methods described herein arrange the geometry of the fluorescent channels 24 and heavy material filter 22, such that the reference detector 18 spectrum becomes independent of beam spot position/movement. Specifically, because the count rates of low and high energy windows of the spectrum define the apparent high voltage of the generator and electron beam current, if the spectrum does not depend on the beam spot movement, the generator parameters are also stabilized to one set of nominal values.

As mentioned above, if the electron beam spot position or shape changes on the radiator target 20, the spectrum in the reference detector 18 may be affected. The beam spot defines the effective photon source geometry. Moving the photon source changes the flux of the photons entering the detector crystal 26 through the filter 22 (e.g., the high energy window counts) if it is not positioned symmetrically. Additionally, the flux of photons entering the fluorescent channel 24 (e.g., the low energy window counts) depends on the solid angle from the photon source to the channel opening. When the counts in the low and high energy windows change, the apparent values of generator parameters may vary.

Figure 5:
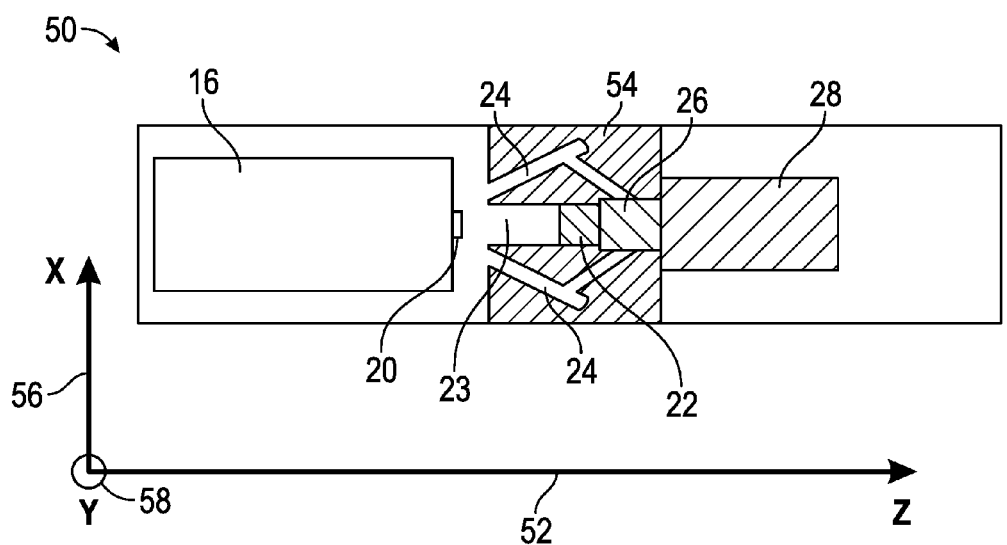
FIG. 5 is a schematic cross section diagram of a well-logging tool that may obtain logging measurements using an X-ray system that is regulated using symmetric fluorescent channels, in accordance with an embodiment.

Accordingly, in one embodiment, a symmetric design of the reference detector block may be used to make the detector spectrum independent of beam spot movement. FIG. 5 illustrates a downhole tool 50 that includes a reference detector 18 with a symmetric design, in accordance with an embodiment. In the embodiment of FIG. 5, the crystal 26 is located along the axis of the electron beam (e.g., the Z axis 52). Accordingly, there are two ways for photons to reach the crystal 26. Specifically, the photons may reach the crystal 26 via the direct channel 23 and/or the fluorescent channels 24. Photons going through the direct channel 23 pass through the filter 22, which may be made from high density materials such as tungsten, lead, etc. The photons passing through the direct channel 23 register as a high energy peak (high energy tail) in the detector spectrum.

In the current embodiment, the target 20, the direct channel 23, the filter 22, and crystal 26 are aligned substantially symmetrically, such that beam spot movement on the target 20 has a negligible effect on the high energy window counts. Further, the width of the direct channel 23 can be increased to reduce the variation of high energy window counts within desired limits. For example, limits on the variation of window counts may be defined by accuracy specifications of the density measurement. These limits may be met by varying the width of the direct channel 23.

In the current embodiment, a heavy metal inner shielding 54 surrounds the detector 18 crystal 26. This shielding 54 may prevent the photons from the wellbore 03 and/or or formation 02 from entering the reference detector 18 crystal 26.

In the current embodiment, the symmetric design includes symmetric fluorescent channels 24 as well. These symmetric fluorescent channels 24 are positioned inside the inner shielding 54. Instead of one path to the detector 18 crystal 26, the current embodiment illustrates two symmetric fluorescent channels 24. The two channels 24 are substantially symmetrically located in the XZ plane (e.g., defined by the X-Axis 56 and the Y-Axis 58) from the electron beam axis (e.g., the Z-axis 52).

The symmetric design of the channels 24 may minimize the variation of spectra and keep it within the predefined limits. For example, because the two channels 24 are substantially symmetrical, if the beam spot moves in the X-direction (e.g., along the X-Axis 56), the flux deficit in one channel is compensated by a flux increase in another channel.

The shape of the channels 24 may vary and the cross section may be circular or rectangular, for example. If the size of the channel 24 cross section is large enough, the beam spot movement in the Y-direction (e.g., along the X-Axis 58) may not strongly affect the low energy window counts. Further, the low energy counts may be stabilized to a desirable factor by adjusting the size of the channels 24. Accordingly, the symmetric design of the two channels 24 may help to stabilize the reference detector 18 spectrum, even when the beam spot on the target 20 moves in the XY plane.

While the current embodiment illustrates two symmetric fluorescent channels 24, other embodiments are not limited to this number of fluorescent channels. If desirable and the geometry of the downhole tool 50 allows, additional channels 24 may be added with azimuthal symmetry. Further, the cross section of each of the channels 24 may be reduced if their number is increased, maintaining the low energy count rates within predefined limits.

In some embodiments, the inner surface of the fluorescent channels 24 may be coated with a different material to change the energy of the fluorescent peak. Further, in some embodiments, tubes, plates, or coatings made by different materials may be placed inside the channels to change the energy of the fluorescent peak.

Figure 6:
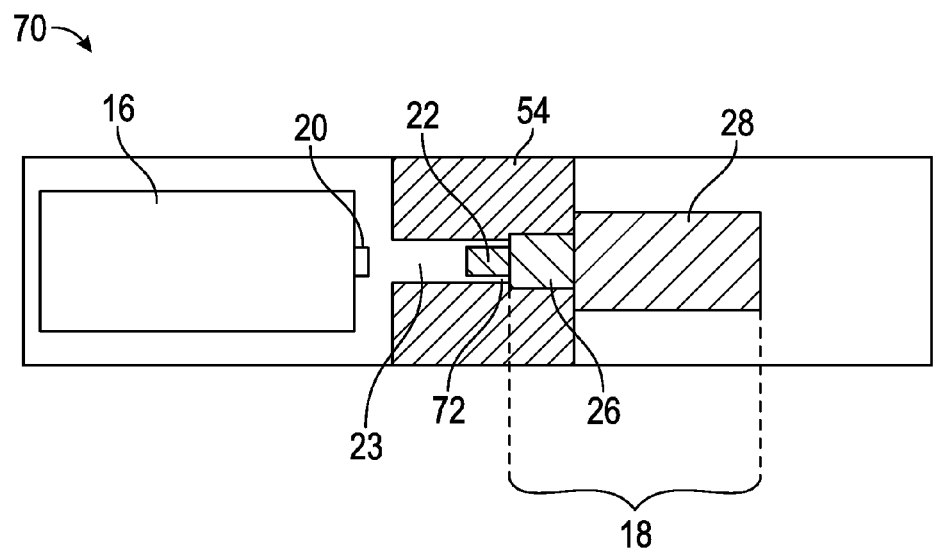
FIG. 6 is a schematic cross section diagram of a well-logging tool that may obtain logging measurements using an X-ray system that is regulated using symmetric gaps as fluorescent channels, in accordance with an embodiment.

Turning now to an alternative embodiment, FIG. 6 illustrates a downhole tool 70 where a narrow gap 72 is formed in the direct channel 23 around the heavy filter 22 material, instead of using the symmetric fluorescent channels 24 of FIG. 5. In the current embodiment, the photons entering into the gap 72 do not have direct path to the detector 18. Accordingly, fluorescent emission occurs on the walls of the direct channel around the filter 22. As illustrated in the cross section 80 of FIG. 7A, the filter 22 may be mounted to the inner shielding 54, leaving empty passages 82 for the fluorescent and scattered photons.

Figure 7A:
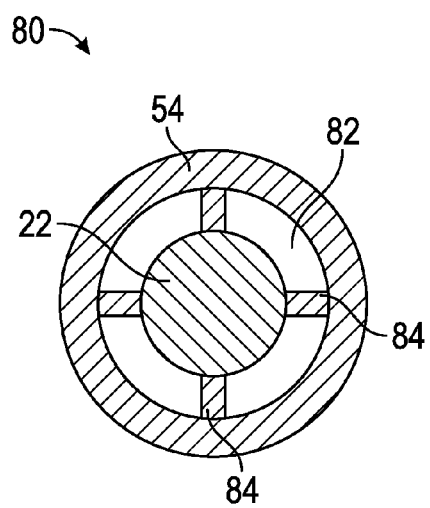
FIGS. 7A and 7B are schematic cross section diagrams of a section of a well-logging tool that may obtain logging measurements using an X-ray system that is regulated using symmetric gaps as fluorescent channels, in accordance with an embodiment.

As illustrated in FIG. 7A, the filter 22 may be connected to the inner shielding 54 by one or more centralizing devices 82. Alternatively, in some embodiments, the inner shielding 54 and filter 22 may be made as one piece leaving an empty area for the fluorescent gap 82 around the filter 22.

Similar to the symmetric channels of the embodiment illustrated in FIG. 5, in operation, when the beam is shifted to one direction perpendicular to the generator 16 axis, the fluorescent flux passing through the gap 82 does not change, because a deficit of photons on one side of the gap is compensated for by an excess of photons on the diametrically opposite side.

Figure 7B:
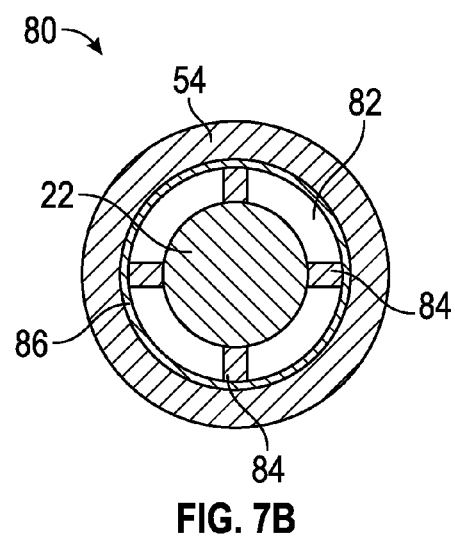

Further, as illustrated in the embodiment of FIG. 7B, to obtain a desired amount of fluorescent photons of a desired energy, the walls of the direct channel 52 may be coated with different materials 86 other than the materials of inner shield and the filter 22. Alternatively, sleeves of different materials may be inserted around the inner diameter of the inner shield 54, the outer diameter of the filter 22, or both.

Figure 8:
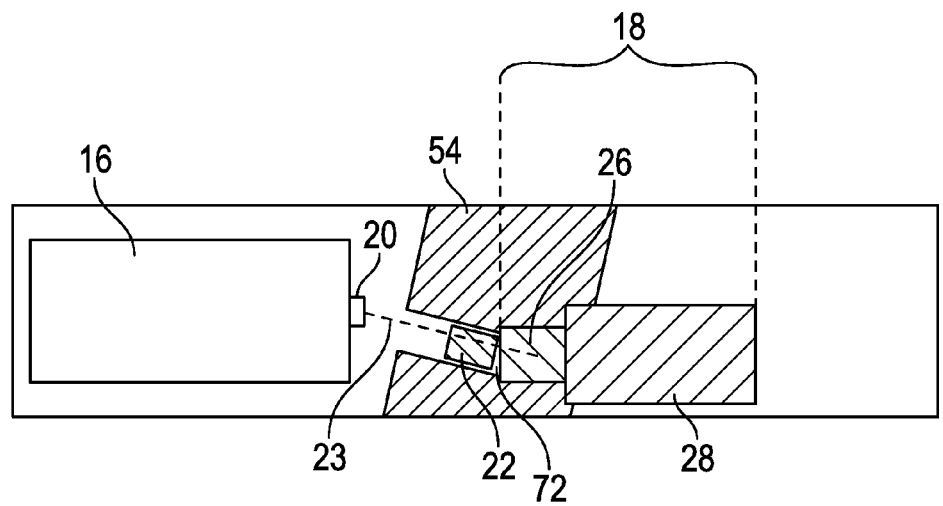
FIG. 8 is a schematic cross section diagram of a well-logging tool that may obtain logging measurements using an X-ray system that is regulated using symmetric gaps as fluorescent channels, where the reference detector crystal is shifted from the electron beam axis, in accordance with an embodiment.

In some embodiments, such as the embodiment depicted in FIG. 8, the gap 72 around the filter 22 may also work when the detector 18 is no longer coaxial with the electron beam axis. In the current embodiment, when the beam spot movement is small enough in comparison to diameter of the direct channel, the variation of low and high energy window counts may remain small enough to keep the window count within desirable tolerance limits. The geometry of the direct channel 23, filter 22 dimensions, and the gap 72 size may be adjusted to keep the uncertainty of detector window counts within the required limits. Further, specific positioning of the crystal 26 may also be adjusted to maintain stable counts.

Angle Based Stabilization

Though the above-described embodiments may help to stabilize output regardless of beam movement, these embodiments may involve complex mechanical designs and associated tight tolerances. Further, the fluorescence material may be the same or substantially the same as the one used for the high energy filter 22 (e.g., tungsten), which may result in the interference from thermal noise, because these material may have a low fluorescent peak. For example, Tungsten has a relatively low fluorescence peak of around 59 keV. In some embodiments, it may be desirable to use a material with a higher fluorescence peak to stay above the thermal noise of the reference detector (especially at high temperature).

Figure 9:
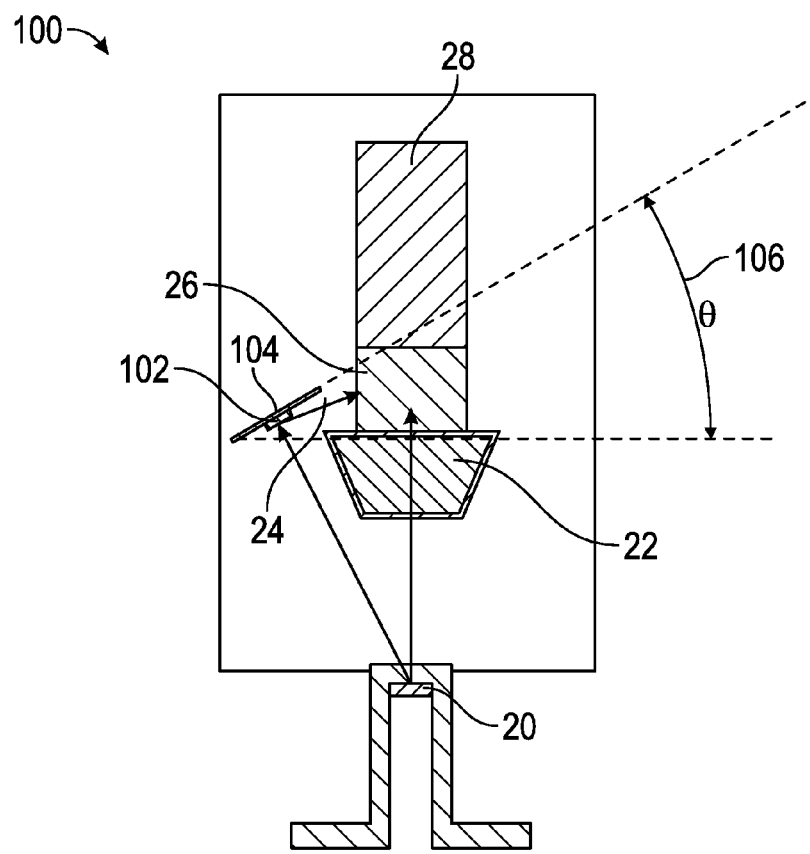
FIG. 9 is a schematic cross section diagram of a well-logging tool that may obtain logging measurements using an X-ray system that is regulated using a non-symmetric design, in accordance with an embodiment.

FIG. 9 illustrates an embodiment of a downhole tool 100 having a single fluorescence channel 24. Specifically, an angle between the target 20 and a fluorescence material structure (e.g., disc 102) may be used to reduce the number of fluorescence channels 24 to a single fluorescence channel 24, while maintaining spectrum stability.

In the current embodiment, the fluorescence material structure (e.g., disc 102) may be constructed of a material with the proper fluorescence energy (e.g., Bismuth or Gold). The fluorescence disc may be mounted on a support structure 104 of the detector 18. In some embodiments, the support structure 104 may not have any particular fluorescent line in the measurement range of energy. Accordingly, using this technique may not require tight tolerances of the fluorescence channel 24. Instead, the mechanical tolerance may be mainly limited to the size of the fluorescent material structure, which, in one embodiment, may be a disc 102.

For example, due to the angle of the fluorescence material structure 102, photons sourced from the target 20 that interact with the fluorescence material structure 102 may be directed through the single fluorescence pathway 24 in an optimized angle 106. By adjusting the fluorescence according to this optimized angle 106, the emitted fluorescence photons may reach the crystal 26, with relatively little dependence on beam spot positioning, as will be discussed in more detail below.

If desired, in some embodiments, the high-energy filter 22 (e.g., a Tungsten filter) may be surrounded with a material that will not generate fluorescence x-rays but still attenuate fluorescence coming from the filter 22.

Figure 10:
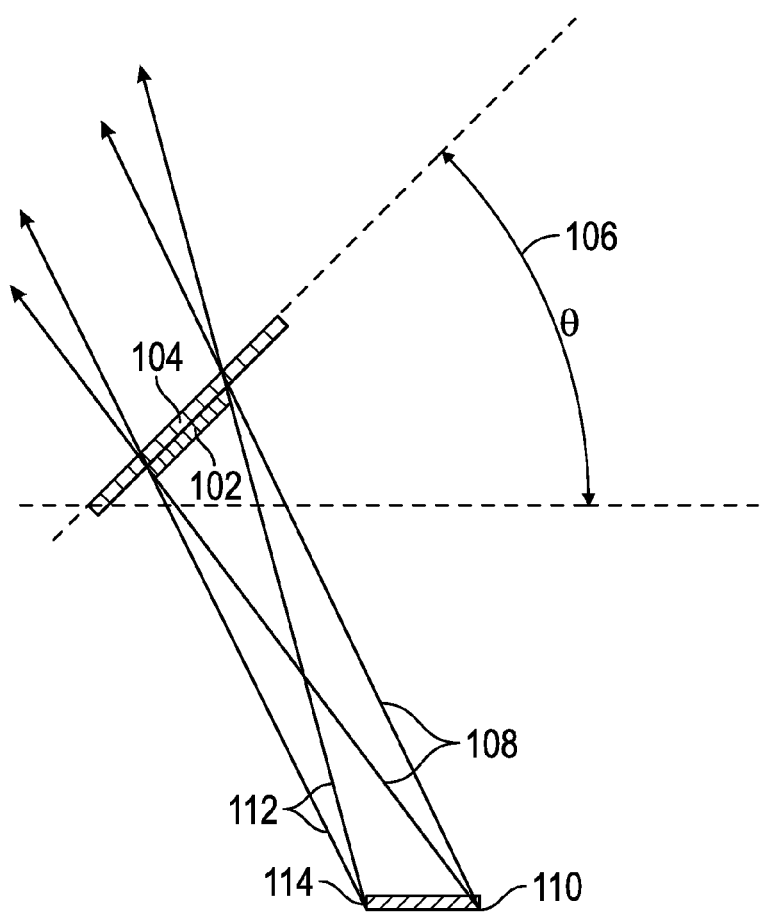
FIG. 10 is a schematic diagram illustrating angular choice resulting in a common solid angle regardless of beam spot location, in accordance with an embodiment.

FIG. 10 is a diagram illustrating an effect of the angular positioning of the fluorescence disc 102 and/or support structure 104. Specifically, the angle between the disc 102 and the target 20 may be optimized in such a way that the solid angle is the same for any beam position on the target 20. For example, beams 108 from a first beam spot 110 may result in fluorescence that follow the same optimized angle 106 as beams 112 from a second beam spot 114. Accordingly, the flux of x-rays generated by the disc 102 fluorescence may not depend on the beam spot location on the target 20.

When the target 20 is not aligned with the crystal 26, a proper tilt angle on the high energy filter 22 can compensate for the effect of a beam spot movement on the low-energy part of the spectrum. Accordingly, in the current embodiment, there is no need for multiple channels. Further, the disc 102 mounted on the support structure 104 may be in the plane of the measurement detectors, which may preserve room in the downhole tool 100. The tolerance can be well controlled and inspected before installing the disc 102 with its support structure 104. For example, the disc 102 with its support structure 104 may be exchanged if a different fluorescence energy is desired.

Channel Manufacturing

In some embodiments, in order to correct for beam spot movement, the size (e.g., cross section) and position of the channels 24 may require a high dimensional accuracy. Channels 24 with this type of tolerance are traditionally drilled and reamed into a high density material to the correct cross-sectional size. Unfortunately, these traditional methods have resulted in the positional variations of the drilled hole, for reasons such as:

Position error in the initial drilling location.
Angle error in the drilled hole.
Position and angle error in the additional holes.
Drill bit movement while starting to drill an angled hole.
Drift of the drilled hole (especially for small diameter holes of long length).

Figure 11:
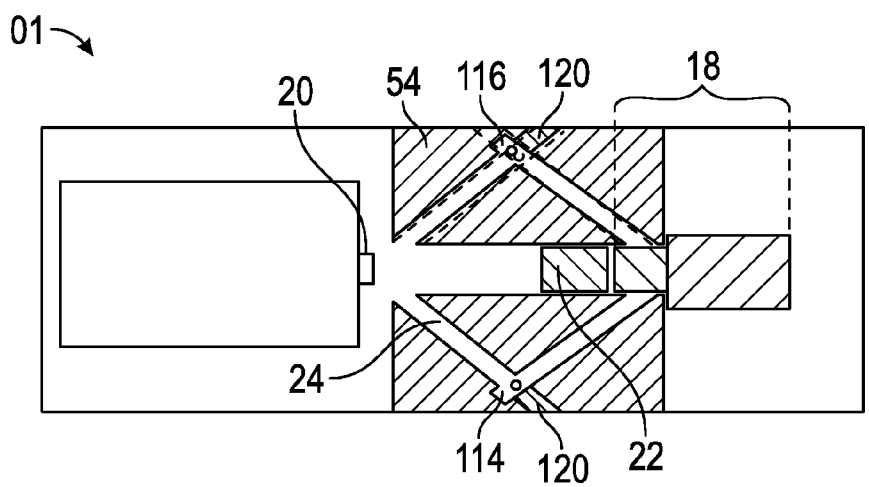
FIG. 11 is a schematic cross section diagram of a well-logging tool where channels are drilled into the tool, in accordance with an embodiment.

FIG. 11 illustrates an embodiment of a tool 01 with traditionally drilled channels. Variations caused by traditional channel drilling may create difficulty in ensuring a positional symmetry with high accuracy. Further, the exact intersection point 114 of the two holes and the exact geometry at the intersection 114 is generally difficult to achieve when the drilling starts in two different locations. Further, it is even more difficult to repeat the same geometry from tool-to-tool. Since the fluorescence occurs at the intersection of the two drilled holes, it is important that this geometry be well-defined and not vary. Additional problems may be introduced by the fact that traditionally drilled channels are hard to inspect after they are made.

As illustrated in FIG. 11, positional uncertainty 116 may be introduced by an angle error in a drilled hole. For example, a hole that is a standard dimension of a fluorescent channel (e.g. 2" long) with a standard angular tolerance (e.g., an angular tolerance of +/−0.5°) may have a lateral drift of as much as +/−0.017 inch (or 0.034 inch total). This is nearly an order of magnitude larger than the positional tolerance useful to correct for beam spot movement. The effect of such channel position due to angular and position tolerance errors can be seen (not to scale) in FIG. 11.

Another problem with drilling four different holes to create these fluorescent channels 24 is that each hole must be drilled along a different axis. In other words, a different setup of the workpiece on the drilling machine may be necessary, which may introduce additional complexity and positional errors. After the holes are drilled from the outside of the part, some of the holes may need to be plugged near the intersection point, in order to give a consistent surface for fluorescent photon emission and to prevent photon leakage to the environment outside of the tool. For example, one set of possible plug locations 120 is shown in FIG. 11. This plugging operation introduces an additional source of error in the manufacturing stage because the plug could be installed to the wrong depth.

As noted above, drilling a series of holes in a part can present manufacturability issues. Further, inspection of all holes as well as the intersection points may be difficult because the position cannot be inspected directly and the drift of the holes can be difficult to measure.

Given the high positional accuracy required for stable X-ray regulation that is independent of beam spot movement, the scrap rate of a part made with drilled fluorescent channels may be high.

The techniques described herein reduce the positional error of the channels 24 by using a different method to manufacture channels along the midplane of a shielded part. As will be appreciated, the channels 24 in this method may be rectangular instead of the circular channels that are produced by traditional drilling.

Figure 12:
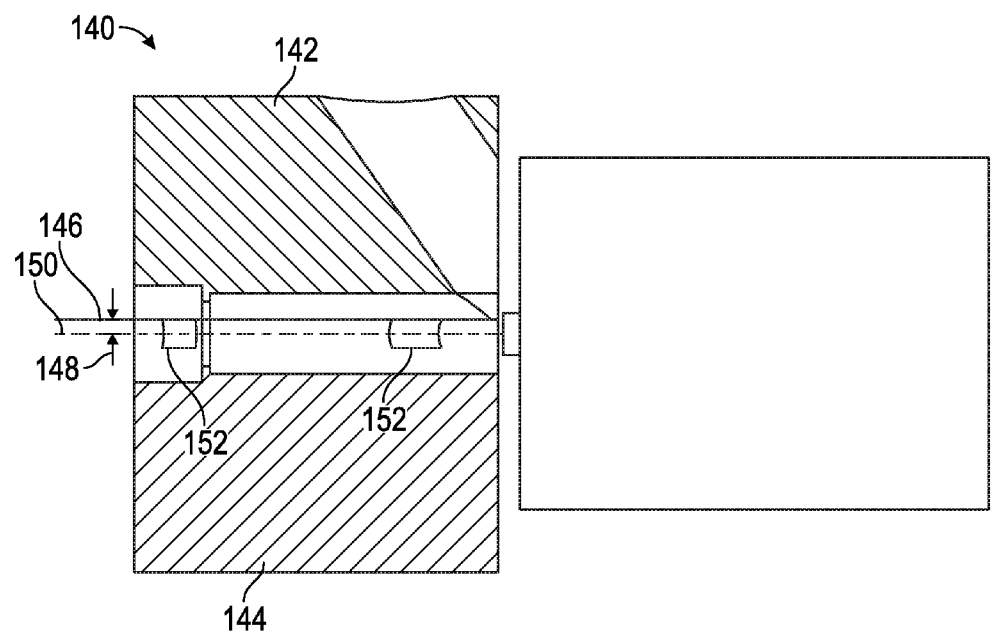
FIG. 12 is a schematic cross section diagram illustrating a well-logging tool manufactured using a split part approach, in accordance with an embodiment.

FIG. 12 illustrates an embodiment of a shield 140 produced as two or more separate pieces (e.g., a top piece 142 and a bottom piece 144), in accordance with an embodiment. The two pieces 142 and 144 are split along a plane 146 at a distance of half the cross-sectional channel height 148 from the electron beam axis 150. The fluorescent channels 152 are milled into the larger part of the shield (in the depicted embodiment of FIG. 12, the bottom piece 144) to a depth of the full cross-sectional channel height.

Using this technique, the entire fluorescent channel 152 geometry may be machined in one milling setup with a typical numerical control (NC) machining position, having tolerances on the order of one one-thousandth of an inch. Accordingly, additional compounding positional errors are not encountered with this technique. Further, since the channels 152 are machined from the top, the drift of the channel 152 along its length will be small, and it is defined by the position tolerance of the milling machine.

Additionally, manufacturing the channels 152 using this technique results in well-defined intersection points of the channels 152 and the positions and sizes of all channels 152 and intersection points may be inspected easily. Channels 152 of this type may not be deep, so the channel cross-section may be machined (e.g., milled) to tight tolerances without bending a bit, which may allow for greater control of the cross-sectional size of the channel 152. Further, since the channels 152 are only located in one of the two pieces of the part, a channel 152 that is incorrectly machined may only result in discarding one of the two pieces instead of the entire part.

Further, since the channels 152 are easily accessible from the top, the channels 152 may be easily filled or coated with an alternate material to change the energy of fluorescence (as discussed above).

Figure 13:
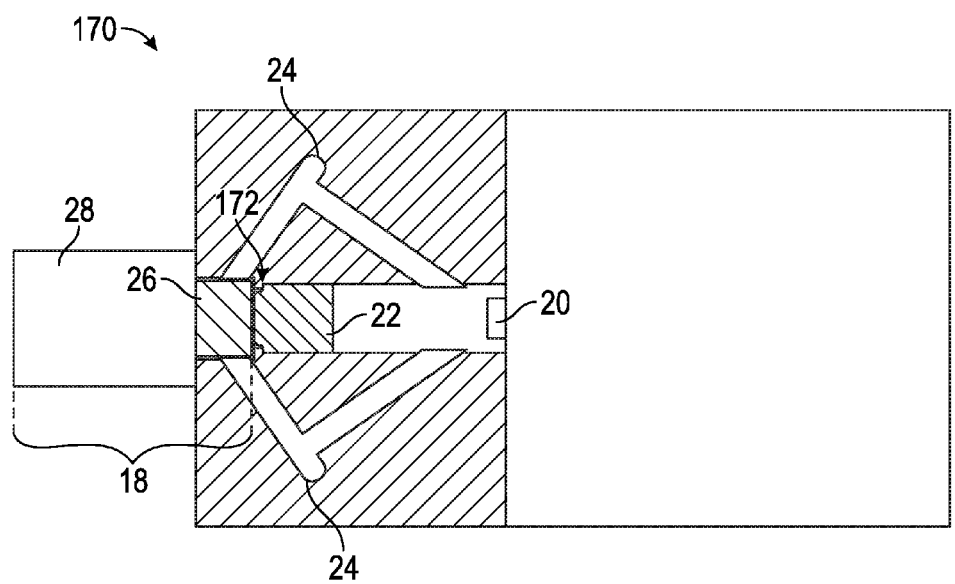
FIG. 13 is a schematic cross section diagram illustrating a well-logging tool where a step on the filter is used to shield leakage photons around the filter, in accordance with an embodiment.

Features in this design prevent direct leakage of photons from the source to the reference detector 18 crystal 26, which may degrade the ability to regulate the X-ray generator 16 effectively. FIG. 13 illustrates an embodiment of a downhole tool 170 that provides such features. First, the high energy filter 22 has a larger diameter than the reference detector 18 crystal 26. Accordingly, photons that leak around the filter 22 or between the two pieces of the shielding do not have a direct path to the crystal 26. Secondly, a step 172 is added to prevent scattered photons from reaching the reference crystal 26.

Figure 14:
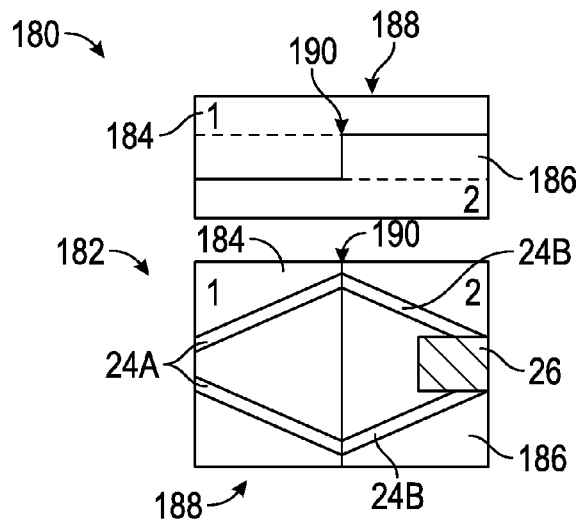
FIG. 14 is a schematic cross section diagram illustrating two halves of a reference detector shielding block of a well-logging tool, in accordance with an embodiment.

The embodiment shown in FIG. 5 prevents the leakage of photons to the crystal 26 through the gap between the two pieces of the shielding. However, leakage is still possible to the fluorescent channels 24 if the surfaces of the two mating shield pieces of this part are not flat or have machining defects. In this case, fluorescence can occur not only close to the channel 24 intersection spot but also by this leakage of photons into the channels 24, which could make a path of fluorescent photons to the crystal 26. Such a contribution to the low energy counts/fluorescent peak is not necessarily symmetrical with this type of leakage. However, the leakage may be completely blocked when an additional step is incorporated with the two pieces. For example, FIG. 14 illustrates a first cross sectional view 180 and second cross sectional view 182 of two halves (first half 184 and second half 186) of a reference detector shielding block 188. The initial channels 24A that go from the target 20 may be machined in one piece (or one step) (e.g., the first half 184) and secondary channels 24B may be machined in the other piece (e.g., the second half 186). The step 190 prevents the photons from leaking through the gap between the two halves 184 and 186 of the block 188.

Figure 15:
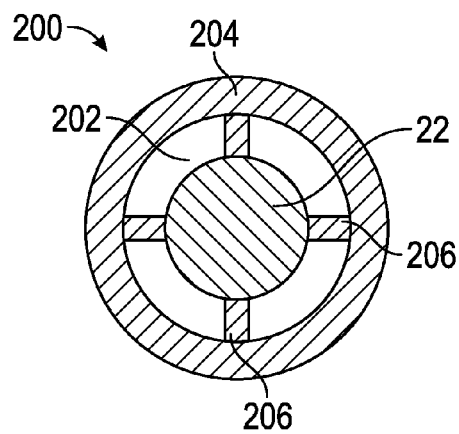
FIG. 15 is schematic cross section diagram of a well-logging tool where symmetric gaps are created by inserting a centralized inner shield, in accordance with an embodiment.
Figure 16:
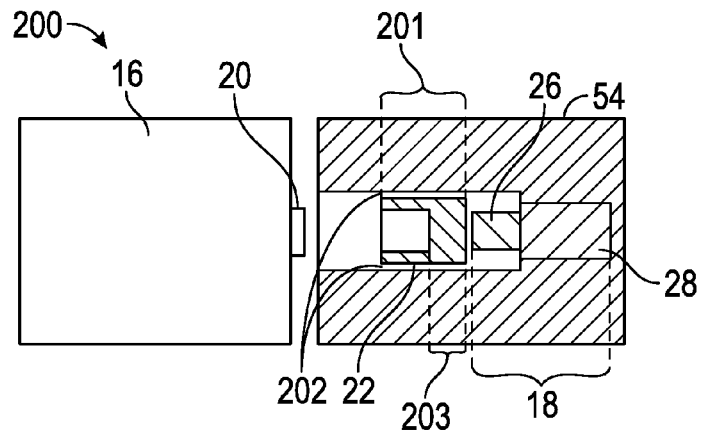
FIG. 16 is a schematic cross section diagram illustrating a well-logging tool having an annular fluorescent channel, in accordance with an embodiment

FIG. 15 illustrates a schematic cross-section of a tool 200 embodiment having a fluorescent gap 202, as described above. This design may be produced by drilling the hole in the inner shield 204, and inserting a precision machined filter 22 that is centralized in the inner shield (e.g., via mounting screws or other centralizing devices 206). A cross-section as viewed from the top of the tool 200 is shown in FIG. 16. The inner diameter of the inner shield 54 and/or the outer diameter of the filter 22 can be coated with an alternate material to change the fluorescent energy.

As illustrated in FIGS. 15 and 16, the form factor of a tool 20 with an annular gap 202 around the filter 22 may reduce sensitivity to diameters of the parts in the assembly, which may make the part easier to manufacture and reduce tool-to-tool variability.

A larger fluorescent gap that is less sensitive to geometric tolerances on the fluorescence annulus may be made, however this may increase the number of low-energy fluorescent photons that reach the reference detector 18 crystal 26. The number of fluorescent photons may be limited by increasing the length 201 of the channel, which may also mean increasing the length 203 of the high energy filter 22. Such a change may decrease the number of high energy photons reaching the reference detector 18 crystal 26. Accordingly, in the current embodiment, a cup-shaped filter 22 is used. This embodiment decouples the length 203 of the high energy filter 22 from the length 201 of the fluorescence annular channel 202, while allowing for greater variance on the tolerance of the inner diameter of the inner shield 54, the outer diameter of the filter 22, as well as the concentric position tolerance of the filter 22 within the inner shield 54.

Each part shown in FIG. 16 is cylindrical and co-axial, however other shapes may be used. The filter 22 and the annular fluorescent channels 24 may be symmetric about an imaginary line between the electron beam spot position at the target 20 (source of photons) and the center of the reference crystal 26. However, it is not necessary for the target 20 and the crystal 26 to be coaxial. This annular design is more compact and is useful for smaller tool 01 diameters than the symmetric channel design mentioned previously.

By regulating X-ray generation in logging tools during a downhole application, more accurate density and/or photoelectric factor measurements may be obtained. Accordingly, controlling a generator 16 of an X-ray system 14 of the logging tool 01 based upon the normalized difference between a plurality of windows of a high energy peak of spectrum data obtained by a reference detector 18, may result in stabilization of the source 16. As a result, increased accuracy in density and/or photoelectric factor measurements may be obtained, enabling decision makers to manage the wellbore 03 to more effectively produce hydrocarbons, complete the well, or perform any other suitable wellbore 03 management.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A downhole tool, comprising:
an X-ray system, comprising:
a generator that produces a source stream of electrons and accelerates them to a beam spot on a target to generate photons;
a reference detector system, comprising:
a photomultiplier tube (PMT) configured to detect and provide an amount and energy of the source stream of photons that reach it;
a detector crystal configured to interact with photons and produce scintillation light before they reach the PMT;
a direct channel configured to allow at least a portion of the stream of photons to directly reach the detector crystal;
a filter configured to reduce a low energy part of a resultant spectrum of the PMT;
a plurality of fluorescent channels positioned substantially symmetrically, such that photon flux entering the reference detector from the fluorescent channels is negligibly impacted by variations of the beam spot.

2. The downhole tool of claim 1, wherein the plurality of fluorescent channels consist of two fluorescent channels.

3. The downhole tool of claim 1, wherein the filter is disposed within the direct channel.

4. The downhole tool of claim 1, comprising an internal shield configured to restrict X-rays reflected from a formation or borehole from reaching the reference detector system.

5. The downhole tool of claim 4, wherein the plurality of fluorescent channels are disposed in the internal shield.

6. The downhole tool of claim 5, wherein one or more surfaces of the fluorescent channels contain inserts or coatings of a different material to affect the energy level of fluorescent photons supplied via the florescence channels.

7. The downhole tool of claim 4, wherein the plurality of fluorescent channels comprise channels formed by one or more gaps between the internal shield and the filter.

8. The downhole tool of claim 7, wherein the filter is centralized inside the inner shield by one or more centralizing devices.

9. The downhole tool of claim 7, wherein one or more surfaces of the fluorescent channels contain inserts or coatings of a different material to affect the energy level of fluorescent photons supplied via the florescence channels.

10. The downhole tool of claim 1, wherein the reference detector system is coaxial with an axis of the accelerated electron beam.

11. The downhole tool of claim 1, wherein the reference detector system is not coaxial with an axis of the accelerated electron beam.

12. A downhole tool, comprising:
an X-ray system, comprising:
a generator that produces a source stream of electrons and accelerates the electrons to a beam spot on a target, where they generate photons;
a reference detector system, comprising:
a photomultiplier tube (PMT) configured to detect and provide an amount and energy of the source stream of photons that reach it;
a detector crystal configured to interact with photons and produce scintillation light before they reach the PMT;
a direct channel configured to allow at least a portion of the stream of photons to directly reach the detector crystal;
a filter configured to reduce a low energy part of a resultant spectrum of the PMT;
a fluorescence material structure positioned and angled to generate fluorescence that reaches the detector crystal via at least one fluorescent channel or aperture, such that a photon flux entering the reference detector via the fluorescent channel or aperture is negligibly impacted by variations in the position or shape of the beam spot.

13. The downhole tool of claim 12, wherein the fluorescence material structure comprises a fluorescent disc.

14. The downhole tool of claim 12, wherein an angle of the fluorescence material structure only allows photons that have been generated by fluorescence in the fluorescence material to reach the crystal of the reference detector.

15. The downhole tool of claim 14, wherein the angle of the fluorescence material structure is configured such that the amount of fluorescence radiation reaching the reference detector is insensitive to variations of the beam spot position or shape.

* * * * *